United States Patent
McAtee et al.

(10) Patent No.: US 6,573,414 B2
(45) Date of Patent: Jun. 3, 2003

(54) METHOD FOR PRODUCING $C_9$-ALCOHOLS AND METHOD FOR THE INTEGRATED PRODUCTION OF $C_9$-ALCOHOLS AND $C_{10}$-ALCOHOLS

(75) Inventors: Michael Richard McAtee, Jackson, TX (US); Rocco Paciello, Bad Dürkheim (DE); Michael-Dieter Ulbrich, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/181,461

(22) PCT Filed: Jan. 26, 2001

(86) PCT No.: PCT/EP01/00854

§ 371 (c)(1),
(2), (4) Date: Jul. 18, 2002

(87) PCT Pub. No.: WO01/55065

PCT Pub. Date: Aug. 2, 2001

(65) Prior Publication Data

US 2003/0022947 A1 Jan. 30, 2003

(30) Foreign Application Priority Data

Jan. 27, 2000 (DE) .......................... 100 03 482

(51) Int. Cl.$^7$ .......................... C07C 27/20; C07C 27/22; C07C 27/24; C07C 29/15; C07C 27/10; C07C 27/12; C07C 27/14; C07C 27/16; C07B 2/102

(52) U.S. Cl. ...................... 568/909; 568/910; 568/910.5

(58) Field of Search ............... 568/909, 910, 568/910.5

(56) References Cited

U.S. PATENT DOCUMENTS 5,849,972 A 12/1998 Vicari

OTHER PUBLICATIONS

Abstract WO 99/25668, May 27, 1999.
Derwent JA–032386.
04036251, Abstracts of Japan.
03044340, Abstracts of Japan, Jun. 2, 1992.
Ind. Org. Chem., 19–24, VCH, 4, 1994, Weisermel et al.
Gusev et al., Nauchno–Issled Ins. Pereab.Nefti (1981) 39, 11–20.
Derwent Abst. JP52132–004.
Yokoyama, Nippon Gasu Kyokjaishi (1978), 31(8), 21–29.

Primary Examiner—Samuel Barts
Assistant Examiner—Eluis O. Price
(74) Attorney, Agent, or Firm—Keil & Weinkauf

(57) ABSTRACT

A process for preparing $C_9$-alcohols comprises a) providing a $C_4$-hydrocarbon stream comprising butene and butane; b) subjecting the $C_4$-hydrocarbon stream to oligomerization over an olefin oligomerization catalyst and fractionating the resulting reaction mixture to give an octene-containing stream and a butene-depleted $C_4$-hydrocarbon stream; c) subjecting the butene-depleted $C_4$-hydrocarbon stream to steam reforming or partial oxidation to give carbon monoxide and hydrogen; d) hydroformylating the octene-containing stream by means of carbon monoxide and hydrogen in the presence of a hydroformylation catalyst to form $C_9$-aldehydes, where the carbon monoxide used and/or the hydrogen used originate at least in part from step c); and e) catalytically hydrogenating the $C_9$-aldehydes by means of hydrogen. In a variant of the process, part of the butenes present in the $C_4$-hydrocarbon stream are hydroformylated to form $C_5$-aldehydes, these are subjected to an aldol condensation and the product of the aldol condensation is hydrogenated to form $C_{10}$-alcohols. The process allows the $C_4$-hydrocarbon stream used to be substantially utilized as material.

15 Claims, No Drawings

METHOD FOR PRODUCING $C_9$-ALCOHOLS AND METHOD FOR THE INTEGRATED PRODUCTION OF $C_9$-ALCOHOLS AND $C_{10}$-ALCOHOLS

The present invention relates to a process for preparing $C_9$-alcohols and also to a process for the integrated preparation of $C_9$-alcohols and $C_{10}$-alcohols.

Fossil fuels and the hydrocarbons obtained therefrom have a double function in industrial synthesis. They serve firstly as energy sources and secondly as raw materials for chemical products. It is frequently customary to burn hydrocarbons obtained as by-products in industrial synthesis or depleted in specific products of value in order to make their energy content available. There is at present a tendency to replace fossil fuels in the energy sector and thus to secure raw materials supply in the long term at a given supply of fossil raw materials. To achieve this, it is necessary to use as much as possible of the components present in the hydrocarbons obtained from fossil raw materials as materials. A difficulty is that hydrocarbon streams are usually obtained as poorly defined mixtures of variable composition in industrial synthesis. The utilization as materials of the components of value present therein frequently founders on the disproportionately high cost of purification or fractionation. It is necessary to devise integrated processes in which the by-products of one process step can be utilized as materials in a further process step without complicated fractionation being required.

It is known that $C_4$ fractions which are available in large quantities both from FCC plants and from steam crackers and consist essentially of a mixture of butene and butane can be subjected to an oligomerization reaction to produce butene oligomers, in particular octenes. Such a process is described, for example, in DE 4 339 713. This reaction gives the butene oligomers and a butene-depleted $C_4$-hydrocarbon stream in which the butenes are diluted by so much butane that the oligomerization of the butenes still present therein is no longer practical.

The octenes are usually hydroformylated to form $C_9$-aldehydes and then hydrogenated to give $C_9$-alcohols. The $C_9$-alcohols have valuable properties as plasticizer alcohols.

The production of synthesis gas by steam reforming or partial oxidation of hydrocarbons is also known (cf. Weissermel, K. and Arpe H. -J., "Industrielle organische Chemie", VCH, 4th Edition, 1994, pages 19–24.

In Sb. Nauchn. Tr.—Vses. Nauchno-Issled Inst. Pererab. Nefti (1981), 39, 11–20, Gusev I. N. et al. report the preparation of hydrogen by catalytic steam reforming of refinery gases comprising hydrogen, $C_{1-4}$-alkanes and about 20% of alkenes. An upstream hydrogenation step is described as being advantageous.

JP 52132-004 describes the preparation of a gas comprising from 50 to 95 mol % of $H_2$, from 1 to 50 mol % of CO, <25 mol % of $CO_2$ and <25 mol % of methane by treating a hydrocarbon with an NiO catalyst in the presence of steam.

In Nippon Gasu Kyokaishi (1978), 31(8), 21–9, Yokoyama, A. reports results on the catalytic reforming of $C_4$-alkanes and a fraction having a high content of $C_4$-alkanes and $C_4$-alkenes.

It is an object of the present invention to provide a process for preparing $C_9$-alcohols and a process for preparing $C_9$-alcohols and $C_{10}$-alcohols which start out from $C_4$-hydrocarbons and allow very substantial utilization of the feed hydrocarbons as materials.

We have found that this object is achieved by using the butene-depleted $C_4$-hydrocarbon stream obtained in butene oligomerization as starting material for the preparation of synthesis gas which can be employed for hydroformylation of the octenes obtained by butene dimerization to form $C_9$-aldehydes and/or of butene to form $C_5$-aldehydes.

The present invention accordingly provides, in a first aspect, a process for preparing $C_9$-alcohols, which comprises a) providing a $C_4$-hydrocarbon stream comprising butene and butane;

b) subjecting the $C_4$-hydrocarbon stream to oligomerization over an olefin oligomerization catalyst and fractionating the resulting reaction mixture to give an octene-containing stream and a butene-depleted $C_4$-hydrocarbon stream;

c) subjecting the butene-depleted $C_4$-hydrocarbon stream to steam reforming or partial oxidation to give carbon monoxide and hydrogen;

d) hydroformylating the octene-containing stream by means of carbon monoxide and hydrogen in the presence of a hydroformylation catalyst to form $C_9$-aldehydes, where the carbon monoxide used and/or the hydrogen used originate at least in part, e.g. to an extent of more than 50%, preferably to an extent of more than 80%, in particular completely, from step c); and e) catalytically hydrogenating the $C_9$-aldehydes by means of hydrogen.

The hydrogen used in step e) preferably originates at least in part, e.g. to an extent of more than 50%, preferably to an extent of more than 80%, in particular completely, from step c).

The "butene-depleted $C_4$-hydrocarbon stream" is depleted in butene compared to the $C_4$-hydrocarbon stream used. The amount of butenes present is reduced by a proportion corresponding to the butene conversion in the oligomerization. In general, the butene content of the butene-depleted $C_4$-hydrocarbon stream is decreased by from 70 to 99%, usually from 80 to 95%, compared to the $C_4$-hydrocarbon stream used. The butene-depleted $C_4$-hydrocarbon stream comprises, for example, from 5 to 70 mol %, usually from 5 to 45 mol %, of butene, with the remainder being essentially butane.

The present invention also provides, in a second aspect, a process for the integrated preparation of $C_9$-alcohols and $C_{10}$-alcohols, which comprises a) providing a $C_4$-hydrocarbon stream comprising butene and butane;

b) hydroformylating the $C_4$-hydrocarbon stream by means of carbon monoxide and hydrogen to form $C_5$-aldehydes, so as to give a first butene-depleted $C_4$-hydrocarbon stream;

c) subjecting the $C_5$-aldehydes to an aldol condensation; and d) catalytically hydrogenating the products of the aldol condensation by means of hydrogen to form $C_{10}$-alcohols;

e) subjecting the first butene-depleted $C_4$-hydrocarbon stream to oligomerization over an olefin oligomerization catalyst and fractionating the resulting reaction mixture to give an octene-containing stream and a second butene-depleted $C_4$-hydrocarbon stream;

f) hydroformylating the octene-containing stream by means of carbon monoxide and hydrogen in the presence of a hydroformylation catalyst to form $C_9$-aldehydes;

g) catalytically hydrogenating the $C_9$-aldehydes by means of hydrogen;

h) subjecting the second butene-depleted $C_4$-hydrocarbon stream to steam reforming or partial oxidation to give carbon monoxide and hydrogen which are recirculated at least in part to step b) and/or step f).

The hydrogen used in step d) and/or in step g) preferably originates at least in part, e.g. to an extent of more than 50%, preferably to an extent of more than 80%, in particular completely, from step d).

The "first butene-depleted $C_4$-hydrocarbon stream" is depleted in butene compared to the $C_4$-hydrocarbon stream used, and the "second butene-depleted $C_4$-hydrocarbon stream" is depleted in butene compared to the first butene-depleted $C_4$-hydrocarbon stream. In general, the butene content of the first butene-depleted $C_4$-hydrocarbon stream is reduced by from 25 to 50%, and that of the second butene-depleted $C_4$-hydrocarbon stream is reduced by from 70 to 99% compared to the first butene-depleted $C_4$-hydrocarbon stream. The first butene-depleted $C_4$-hydrocarbon stream comprises, for example, from 30 to 60 mol % of butene and the second butene-depleted $C_4$-hydrocarbon stream comprises, for example, from 0.3 to 20 mol % of butene, with the remainder essentially butane.

$C_4$-hydrocarbon streams suitable as starting material comprise, for example, from 50 to 99 mol %, preferably from 60 to 90 mol %, of butenes and from 1 to 50 mol %, preferably from 10 to 40 mol %, of butanes. The butene fraction preferably comprises from 40 to 60 mol % of 1-butene, from 20 to 30 mol % of 2-butene and less than 5 mol %, in particular less than 3 mol %, of isobutene (based on the butene fraction). A particularly preferred starting material is raffinate II, which is an isobutene-depleted $C_4$-fraction from an FCC plant or a steam cracker. Raffinate II has the following typical composition:

| i-,n-butane | 26 mol % |
|---|---|
| i-butene | 1 mol % |
| l-butene | 26 mol % |
| trans-2-butene | 31 mol % |
| cis-2-butene | 16 mol % |

If diolefins or alkynes are present in the $C_4$-hydrocarbon stream, they are preferably removed to leave a residual concentration of less than 10 ppm, in particular less than 5 ppm, prior to the oligomerization. They are preferably removed by selective hydrogenation, e.g. as described in EP-81 041 and DE-1 568 542. In addition, oxygen-containing compounds such as alcohols, aldehydes, ketones and ethers are also preferably substantially removed. For this purpose, the $C_4$-hydrocarbon stream can advantageously be passed over an adsorbent, e.g. molecular sieves, in particular molecular sieves having a pore diameter of from >4 Å to 5 Å.

The individual steps of the process of the present invention are known per se and their specific configuration is not a subject matter of the present invention. The individual steps are described in more detail below with the aid of illustrative or preferred embodiments.

Oligomerization

A number of processes are known for the oligomerization, in particular dimerization, of lower olefins such as butenes.

Each of the known processes is suitable in principle for carrying out the butene oligomerization step of the process of the present invention.

The oligomerization of olefins can be carried out in the presence of homogeneous or heterogeneous catalysts. An example of a homogeneously catalyzed process is the DIMERSOL process. In the DIMERSOL process (cf. Revue de l'Institut Frangais du Petrol, Vol. 37, No. 5, September/October 1982, page 639ff), lower olefins are dimerized in the liquid phase. Suitable precursors of the catalytically active species are, for example, (i) the system $\pi$-allyl-nickel/phosphine/aluminum halide, (ii) Ni(O) compounds in combination with Lewis acids, e.g. $Ni(COD)_2+AX_n$ or $Ni(CO)_2(PR_3)+AX_n$, or (iii) Ni(II) complexes in combination with alkylaluminum halides, e.g. $NiX_2(PR_3)_2+Al_2Et_3Cl_3$ or $Ni(OCOR)_2+AlEtCl_2$ (where COD=1,5-cyclooctadiene, X=Cl, Br, I; R=alkyl, phenyl; $AX_n=AlCl_3$, $BF_3$, $SbF_5$ etc.). A disadvantage of the homogeneously catalyzed processes is the difficulty of removing the catalyst.

These disadvantages do not exist in heterogeneously catalyzed processes. In these processes, an olefin-containing stream is generally passed at elevated temperature over a fixed bed of the heterogeneous catalyst.

A widespread industrial process is the UOP process using $H_3PO_4/SiO_2$ in a fixed bed (cf., for example, U.S. Pat. No. 4,209,652, U.S. Pat. No. 4,229,586, U.S. Pat. No. 4,393,259). In the Bayer process, acid ion exchangers are used as catalyst (cf., for example, DE 195 35 503, EP-48 893). WO 96/24567 (Exxon) describes the use of zeolites as oligomerization catalysts. Ion exchangers such as Amberlite are also used in the Texas Petrochemicals process (cf. DE 3 140 153).

The dimerization-of lower olefins using alkali metal catalysts is also known (cf. Catalysis Today, 1990, 6, p. 329ff).

For the present purposes, preference is given to carrying out the butene oligomerization over a heterogeneous nickel-containing catalyst. The heterogeneous, nickel-containing catalysts which can be used may have different structures, with preference being given to catalysts comprising nickel oxide. Catalysts known per se, as are described in C. T. O'Connor et al., Catalysis Today, Volume 6 (1990), pages 336–338, can be used. In particular, supported nickel catalysts are used. The support materials can be, for example, silica, alumina, aluminosilicates, aluminosilicates having sheet structures and zeolites, zirconium oxide, which may have been treated with acids, or sulfated titanium dioxide. Particularly useful catalysts are precipitated catalysts which are obtainable by mixing aqueous solutions of nickel salts and silicates, e.g. sodium silicate with nickel nitrate, and possibly aluminum salts such as aluminum nitrate, and calcining the precipitate. It is also possible to use catalysts which are obtained by intercalation of $Ni^{2+}$ions into natural or synthetic sheet silicates, e.g. montmorillonites, by means of ion exchange. Suitable catalysts can also be obtained by impregnation of silica, alumina or aluminosilicates with aqueous solutions of soluble nickel salts, e.g. nickel nitrate, nickel sulfate or nickel chloride, and subsequent calcination.

Particular preference is given to catalysts which consist essentially of NiO, $SiO_2$, $TiO_2$ and/or $ZrO_2$ and, if desired, $Al_2O_3$. They lead to dimerization occurring preferentially over the formation of higher oligomers and give predominantly linear products. The most preferred catalyst is one which comprises as essential active constituents from 10 to 70% by weight of nickel oxide, from 5 to 30% by weight of titanium dioxide and/or zirconium dioxide, from 0 to 20% by weight of aluminum oxide and silicon dioxide as balance.

Such a catalyst is obtainable by precipitation of the catalyst composition at a pH of from 5 to 9 by adding an aqueous solution of nickel nitrate to an alkali metal water glass solution containing titanium dioxide and/or zirconium dioxide, filtration, drying and heat treatment at from 350 to 6505C. For details of the production of these catalysts, reference may be made to DE 4 339 713. The disclosure of this publication and the prior art cited therein is fully incorporated by reference.

The catalyst is preferably in pelletized or granulated form, e.g. in the form of pellets having, for example, a diameter of from 2 to 6 mm and a height of from 3 to 5 mm, rings having, for example, an external diameter of from 5 to 7 mm, a height of from 2 to 5 mm and a hole diameter of from 2 to 3 mm, or extrudates of various lengths having a diameter of, for example, from 1.5 to 5 mm. Such shapes are obtained in a manner known per se by tableting or extrusion, usually using a tableting aid such as graphite or stearic acid.

The oligomerization over the heterogeneous, nickel-containing catalyst is preferably carried out at from 30 to 280° C., in particular from 30 to 140° C. and particularly preferably from 40 to 130° C. It is preferably carried out at a pressure of from 10 to 300 bar, in particular from 15 to 100 bar and particularly preferably from 20 to 80 bar. The pressure is advantageously set so that the $C_4$-hydrocarbon stream is in the liquid or supercritical state at the temperature selected.

The $C_4$-hydrocarbon stream is advantageously passed over one or more fixed-bed catalysts. Suitable reaction apparatuses for bringing the $C_4$-hydrocarbon stream into contact with the heterogeneous catalyst are known to those skilled in the art. Examples of suitable apparatuses are shell-and -tube reactors or shaft ovens. Owing to the lower capital costs, shaft ovens are preferred. The oligomerization can be carried out in a single reactor, in which case the oligomerization catalyst can be arranged in one or more fixed beds in the reactor. As an alternative, the oligomerization can be carried out using a reactor cascade comprising a plurality of reactors, preferably 2 reactors, connected in series, in which case the oligomerization of the $C_4$-hydrocarbon stream is carried out only to partial conversion during passage through the reactor or reactors upstream of the last reactor of the cascade and the desired final conversion is achieved only during passage of the reaction mixture through the last reactor of the cascade.

After leaving the reactor or the last reactor of a cascade, the reaction mixture is fractionated into an octene-containing stream, possibly higher oligomers and a butene-depleted $C_4$-hydrocarbon stream. The octene-containing stream preferably comprises more than 97% by weight of isomeric octenes; in particular, it consists essentially entirely of isomeric octenes.

The above description of olefin oligomerization applies analogously to the use of the first butene-depleted $C_4$-hydrocarbon stream according to the second aspect of the invention.

Steam Reforming

In steam reforming (allothermal steam cracking), hydrocarbons are cracked catalytically in the presence of $H_2O$ to give a mixture of carbon monoxide and hydrogen, viz. synthesis gas. The heat required for the endothermic reaction is supplied from outside. The chemical reaction in steam reforming can be described by the following overall equation:

$$CH_x + H_2O \rightarrow CO + H_2 + x/2\ H_2$$

From this equation, it can be seen that the contribution of the hydrocarbon feedstock to the amount of $H_2$ formed increases with its hydrogen content. A butene-depleted $C_4$-hydrocarbon stream obtained in the process of the present invention has, for example, a typical composition of 19 mol % of butene and 81 mol % of butane. In this case, the butene-depleted $C_4$-hydrocarbon stream has an average empirical formula of $C_4H_{9.62}$, so that the reaction is:

$$C_4H_{9.62} + 4\ H_2O \rightarrow 4\ CO + 8.81\ H_2$$

The $H_2$/CO molar ratio of the synthesis gas obtained is thus 2.2:1.

The hydroformylation step of the process of the present invention, which is described in more detail further below, can be represented by the following equation:

$$C_8H_{16} + CO + H_2 \rightarrow C_8H_{17}\text{---CHO}$$

and the hydrogenation step by the following equation:

$$C_8H_{17}\text{---CHO} + H_2 \rightarrow C_8H_{17}\text{---CH}_2\text{OH}$$

It can be seen that the combination of the hydroformylation and hydrogenation steps requires hydrogen and carbon monoxide in a molar ratio of 2:1. As shown above, the synthesis gas obtained by steam reforming of the butene-depleted $C_4$-hydrocarbon stream has a well-matched $H_2$:CO molar ratio.

Steam reforming is generally carried out by continuously reacting a mixture of hydrocarbon and steam in externally heated tubes over suitable catalysts, e.g. nickel catalysts, at atmospheric or superatmospheric pressure and temperatures of, for example, from 700 to 950° C. Many parallel, catalyst-filled tubes, usually of chromium-nickel steel, are installed vertically in refractory-lined reactors in such a way that they can expand freely. The tube diameter is, for example, from 15 to 20 cm and the heated tube length is 9 m. The tubes are heated from the outside by means of burners. For heating the tubes, it is possible to use an external fuel or preferably part of the butene-depleted $C_4$-hydrocarbon. To produce low-methane synthesis gas, the gas from the multitube furnace can be passed into an after-combustion furnace configured as a shaft furnace.

Suitable catalysts for steam reforming are described, for example, in Max Appl, Modern Production Technologies, published by Nitrogen, British Sulphur Publishing, 1997, p. 10ff.

The $CO_2$ formed as by-product can advantageously be separated off (see below) and recirculated wholly or in part to the steam reformer. The recirculated carbon dioxide reacts with the hydrocarbons $CH_x$ to form usable hydrogen and carbon monoxide.

In a preferred embodiment, the steam reforming step includes partial or complete hydrogenation of the butene-depleted $C_4$-hydrocarbon stream in order to convert the butene still present wholly or partly into butane before the $C_4$-hydrocarbon stream is introduced into the reformer. The butene content of the stream is preferably reduced to less than 5 mol %, in particular to less than 1 mol %, in this way. The hydrogenation avoids the risk of deposition of carbon on the reforming catalyst, which is possible in the case of a high residual butene content or a high space velocity over the catalyst. Although the deposition of carbon can also be reduced by means of higher steam/hydrocarbon ratio, this is at the expense of the thermal efficiency and the carbon monoxide content of the final gas. The prior hydrogenation of the butene-depleted $C_4$-hydrocarbon stream is advantageously carried out using recirculated hydrogen gas. Hydrogen can be isolated from the synthesis gas formed in steam reforming by, for example, pressure swing adsorption or low-temperature distillation. Such processes are described, for example, in Max Appl, loc. cit., p. 108ff. Suitable plants for producing synthesis gas by steam reforming are described, for example, in Max Appl, loc. cit., p. 7ff.

Suitable catalysts for the complete or partial hydrogenation of the butene-depleted $C_4$-hydrocarbon stream are, for example, nickel oxide, cobalt oxide and/or molybdenum oxide on support materials comprising aluminum oxide.

In a preferred embodiment, a prereforming step is carried out prior to steam reforming or between hydrogenation and steam reforming. The prereformer operates at a lower temperature than the actual steam reformer. Typical operating temperatures of the prereformer are from 400 to 550° C. For this purpose, the mixture of hydrocarbon and steam is passed over the fixed bed of a prereforming catalyst at, for example, 530° C. In the prereformer, higher hydrocarbons, predominantly $C_4$ building blocks, are cracked into $C_2$ and $C_1$ building blocks. Owing to the endothermic reaction, a pressure drop of, for example, from 60 to 70° C. occurs in the catalyst bed. The gas leaving the prereformer is subsequently brought back to the required reformer inlet temperature.

The prereforming step can be carried out in a manner analogous to that described, for example, in H. Jockel, B. Triebskorn: "Gasynthan process for SNG", Hydrocarbon processing, January 1973, pp. 93–98. A suitable prereforming catalyst is a supported nickel oxide catalyst as sold by BASF AG, Ludwigshafen, under the designation G 1-80.

Partial Oxidation

Synthesis gas can likewise be prepared by reacting hydrocarbons with substoichiometric amounts of oxygen. The preparation of synthesis gas by partial oxidation can be described by the following equation:

$$CH_x + \tfrac{1}{2} O_2 \rightarrow CO + x/2\, H_2$$

For a typical empirical formula of the butene-depleted $C_4$-hydrocarbon stream of $C_4H_{9.62}$, this becomes:

$$C_4H_{9.62} + 2\, O_2 \rightarrow 4\, CO + 4.81\, H_2$$

The $H_2/CO$ molar ratio of the synthesis gas obtained is 1.2:1. Synthesis gas of this composition is well-suited to carrying out hydroformylations without hydrogenation. For hydroformylation together with hydrogenation, higher $H_2/CO$ ratios are required. These can be obtained by converting, as explained further below.

In general, the partial oxidation is carried out by preheating the hydrocarbons, oxygen and, if appropriate, steam separately from one another and introducing them via one or more burners into the upper part of a reactor. The burners allow rapid and intimate mixing of the reactants. The preheated feedstocks react in the absence of catalysts at from about 30 to 80 bar and from 1200 to 1500° C. in the combustion zone of the reactor. The heat generated serves for the steam cracking of the hydrocarbons. The gas leaving the reactor is cooled either directly by quenching with water or indirectly by heat exchange. A small part of the hydrocarbons is usually converted into soot. This is generally removed from the synthesis gas by scrubbing with $H_2O$.

Suitable plants for producing synthesis gas by partial oxidation are described, for example, in Max Appl, loc. cit., p. 106ff.

The above descriptions of steam reforming and partial oxidation apply analogously to the use of the second butene-depleted $C_4$-hydrocarbon stream according to the second aspect of the invention.

After-treatment of the Synthesis Gas

A desired carbon monoxide/hydrogen ratio in a synthesis gas can be set by converting over suitable catalysts in the presence of steam. Converting can be employed, in particular, for increasing the $H_2/CO$ molar ratio in a synthesis gas produced by partial oxidation. The underlying reaction between carbon monoxide and steam to give carbon dioxide and hydrogen is an equilibrium reaction:

$$CO + H_2O \leftrightharpoons CO_2 + H_2$$

The reaction is exothermic, so that lower temperatures shift the equilibrium to the right-hand side. Converting can be carried out in one or more stages, e.g. at from 350 to 570° C. and atmospheric pressure or superatmospheric pressure, in the presence of catalysts. Suitable converting catalysts generally comprise Fe—Cr oxide mixtures. These allow the CO content to be, if desired, reduced to about 3 to 4% by volume. In this way, it possible to prepare essentially pure hydrogen which is, for example, suitable for the hydrogenation steps of the process of the present invention.

Carbon dioxide can be removed by scrubbing with suitable solvents. Suitable methods are, for example, pressure water scrubbing and potassium carbonate scrubbing. Further advantageous methods are gas scrubbing with monoethanolamine and diethanolamine (cf. Ullmann's Encyclopedia of Industrial Chemistry, 5th Edition, Volume A12, p. 197).

An overview of suitable methods of removing carbon dioxide may also be found in Max Appl, loc. cit., p. 106ff.

Hydroformylation

Hydroformylation or the oxo process is used to prepare aldehydes from olefins and synthesis gas, i.e. a mixture of carbon monoxide and hydrogen. The aldehydes obtained can, if desired, be hydrogenated by means of hydrogen in the same process step or subsequently in a separate hydrogenation step to form the corresponding alcohols. The hydroformylation is carried out in the presence of catalysts which are homogeneously dissolved in the reaction medium. Catalysts used here are, in general, compounds or complexes of metals of transition group VIII, especially Co, Rh, Ir, Pd, Pt or Ru compounds or complexes which can be unmodified or modified with, for example, amine- or phosphine-containing compounds. A review of processes carried out industrially may be found in J. Falbe, "New Synthesis with Carbon Monoxide", Springer-Verlag 1980, page 162ff.

Hydroformylation of Octenes

While short-chain olefins are at present hydroformylated using predominantly ligand-modified rhodium carbonyls as catalysts, cobalt assumes a dominant role as catalytically active central atom in the case of longer-chain olefins, e.g. octenes. This is due, firstly, to the high catalytic activity of the cobalt carbonyl catalyst regardless of the position of the olefinic double bonds, the branching structure and the purity of the olefin to be reacted. Secondly, the cobalt catalyst can be separated comparatively easily from the hydroformylation products and be recirculated to the hydroformylation reaction. A particularly advantageous process for the hydroformylation of octenes comprises a) bringing an aqueous cobalt(II) salt solution into intimate contact with hydrogen and carbon monoxide to form a hydroformylation-active cobalt catalyst; bringing the aqueous phase containing the cobalt catalyst into intimate contact with the octenes together with hydrogen and carbon monoxide in at least one reaction zone, with the cobalt catalyst being extracted into the organic phase and the octenes being hydroformylated, b) treating the output from the reaction zone with oxygen in the presence of acidic aqueous cobalt(II) salt solution, with the cobalt catalyst being decomposed to form cobalt(II) salts and the latter being back-extracted into the aqueous phase; and subsequently separating the phases;

c) returning the aqueous cobalt(II) salt solution to step a).

Suitable cobalt(II) salts are, in particular, cobalt carboxylates, e.g. cobalt(II) formate, cobalt(II) acetate or cobalt ethylhexanoate, and cobalt acetylacetonate. The catalyst formation can be carried out simultaneously with the catalyst extraction and hydroformylation in one step in the reaction zone of the hydroformylation reaction or in a preceding step (precarbonylation). Precarbonylation can advantageously be carried out as described in DE-A 2 139 630. The resulting aqueous solution of cobalt(II) salts and cobalt catalyst is then introduced together with the octenes to be hydroformylated and hydrogen and carbon monoxide into the reaction zone. However, in many cases it is preferable to carry out the formation of the cobalt catalyst, the extraction of the cobalt catalyst into the organic phase and the hydroformylation in one step by bringing the aqueous cobalt(II) salt solution into intimate contact with the olefins in the reaction zone under hydroformylation conditions. Here, the starting materials are introduced into the reaction zone in such a way that good phase mixing occurs and a very high phase transfer area is generated. Mixing nozzles for multiphase systems are particularly suitable for this purpose.

After leaving the reaction zone, the reaction mixture is depressurized and passed to the cobalt removal step. In the cobalt removal step, the reaction mixture is freed of cobalt carbonyl complexes by means of air and oxygen in the presence of aqueous, slightly acidic cobalt(II) salt solution. In the cobalt removal step, the hydroformylation-active cobalt catalyst is decomposed to form cobalt(II) salts. The cobalt(II) salts are back-extracted into the aqueous phase. The aqueous cobalt(II) salt solution can subsequently be returned to the reaction zone or the catalyst formation step.

The crude hydroformylation product can be fed directly to the hydrogenation step, or, alternatively, the pure $C_9$-aldehydes can be isolated by known methods, e.g. by distillation.

Hydroformylation of Butenes

The second aspect of the invention provides for the hydroformylation of part of the butenes present in the $C_4$-hydrocarbon stream used, before the butene-depleted $C_4$-hydrocarbon stream obtained here (also referred to as "first butene-depleted $C_4$-hydrocarbon stream" to distinguish it from other butene-depleted $C_4$-hydrocarbon streams occurring in the process of the present invention) is passed to butene dimerization.

The hydroformylation of a hydrocarbon stream comprising 1-butene, 2-butene and possibly isobutene gives $C_5$-aldehydes, i.e. n-valeraldehyde, 2-methylbutanal and possibly 2,2-dimethylpropanal. The butene hydroformylation is preferably carried out in the presence of a rhodium catalyst complex in conjunction with a triorganophosphine ligand. The triorganophosphine ligand can be a trialkylphosphine such as tributylphosphine, an alkyldiarylphosphine such as butyldiphenylphosphine or an aryldialkylphosphine such as phenyldibutylphosphine. However, particular preference is given to triarylphosphine ligands such as triphenylphosphine, tri-p-tolylphosphine, trinaphthylphosphine, phenyldinaphthylphosphine, diphenylnaphthylphosphine, tri(p-methoxyphenyl) phosphine, tri(p-cyanophenyl)phosphine, tri(p-nitrophenyl) phosphine, p-N,N-dimethylaminophenylbisphenylphosphine and the like. Triphenylphosphine is most preferred.

The butene hydroformylation is preferably carried out under conditions under which the reaction of 1-butene occurs quickly while the hydroformylation of 2-butene and isobutene occurs slowly. In this way, it is possible for essentially only 1-butene to be converted into n-valeraldehyde and 2-methylbutanal in the hydroformylation.while the 2-butene and any isobutene present are recovered essentially unchanged. This gives a butene-depleted $C_4$-hydrocarboh stream whose 1-butene content is reduced compared to the $C_4$-hydrocarbon stream used and which comprises essentially the original amounts of 2-butene and isobutene which were present in the $C_4$-hydrocarbon stream used. The ratio of n-valeraldehyde to 2-methylbutanal in the $C_5$-aldehydes obtained is preferably at least 4:1, in particular at least 8:1.

The preferential hydroformylation of 1-butene over 2-butene and isobutene can be achieved by using a large excess of triorganophosphorus ligands and by careful control of the temperatures and partial pressures of the reactants and/or products. Thus, the triorganophosphine ligand is preferably used in an amount of at least 100 mol per gram atom of rhodium. The temperature is preferably in the range from 80 to 130° C., the total pressure is preferably not more than 5000 kPa and the partial pressure-of carbon monoxide is kept below 150 kPa and that of hydrogen is kept in the range from 100 to 800 kPa. A suitable hydroformylation process in which a mixture of butenes is used is described in EP 0 016 286.

Hydrogenation

The hydrogenation of the $C_9$-aldehydes to form the $C_9$-alcohols can in principle be carried out using the same catalysts as in the hydroformylatibn, usually at higher temperature. However, preference is generally given to more selective hydrogenation catalysts which are used in a separate hydrogenation step. Suitable hydrogenation catalysts are generally transition metals such as Cr, Mo, W, Fe, Rh, Co, Ni, Pd, Rt, Ru, etc., or mixtures thereof which can be applied to supports, e.g. activated carbon, aluminum oxide, kieselguhr,.etc., to increase the activity and stability. To increase the catalytic activity, Fe, Co and preferably Ni can also be used in the form of the Raney catalysts, viz. as metal sponge having a very high surface area. The hydrogenation of the $C_9$-aldehydes is carried out under conditions which depend on the activity of the catalyst, preferably at elevated temperatures and superatmospheric pressure. The hydrogenation temperature is preferably from about 80 to 250° C., while the pressure is preferably from about 50 to 350 bar.

The crude hydrogenation product can be worked up by customary methods, e.g. by distillation, to give the $C_9$-alcohols.

The hydrogen required for the hydrogenation preferably originates at least in part from the synthesis gas obtained by steam reforming or partial oxidation of the butene-depleted $C_4$-hydrocarbon stream. The hydrogen can be isolated by methods known per se, for example pressure swing adsorption (PSA) or low-temperature distillation (cf. Max Appl, loc. cit., p. 108ff).

Aldol Condensation

Two molecules of $C_5$-aldehyde can be condensed to form α,β-unsaturated $C_{10}$-aldehydes, in particular 2-propyl-2-heptenal and 2-propyl-4-methyl-2-hexenal. The aldol condensation is carried out in a manner known per se, e.g. by action of an aqueous base such as sodium hydroxide or potassium hydroxide. As an alternative, it is also possible to use a heterogeneous basic catalyst such as magnesium oxide and/or aluminum oxide (cf. for example, EP-A 792 862).

The product of the aldol condensation is then catalytically hydrogenated by means of hydrogen to form $C_{10}$-alcohols, in particular 2-propylheptanol and 2-propyl-4-methylhexanol. The above description of the hydrogenation of the $C_9$-aldehydes applies analogously to the hydrogenation of the aldol condensation products.

The invention will now be illustrated by the following examples, which are partly based on simulation calculations. The simulation calculations were carried out using the ASPENPLUS simulation program from ASPEN Tech. By means of this simulation program, the thermodynamic equilibrium established during steam reforming or partial oxidation of a given hydrocarbon stream under particular conditions was calculated. The thermodynamic equilibrium is generally achieved approximately when using catalysts as are employed in industrial practice. The simulation was carried out on the bases of process temperatures and pressures as are customarily employed in the steam reforming or partial oxidation of hydrocarbons.

EXAMPLE 1

A $C_4$-hydrocarbon stream comprising 88 mol % of butene and 12 mol % of butane is passed at 20 bar and 80° C. over a catalyst bed in an adiabatic reactor (length: 4 m, diameter: 80 cm). The catalyst had been produced as described in DE 4 339 713 in the form of pellets having dimensions of 5×5 mm (composition in mol % of active components: Nio 50 mol %, $TiO_2$ 12.5 mol %, $SiO_2$ 33.5 mol %, $Al_2O_3$ 4 mol %).

The octenes and higher butene oligomers formed were separated from the output from the reactor. The resulting butene-depleted $C_4$-hydrocarbon mixture comprised 80.5 mol % of butane and 19.5 mol % of butene, corresponding to a butene conversion of 95%.

In a simulation calculation, the synthesis gas composition expected in the steam reforming of this butene-depleted $C_4$-hydrocarbon stream was calculated. The following parameters were employed:

S/C =2.5
(S/C=mol of steam used for steam reforming per mol of C present in the $C_4$ feed mixture)
Reformer outlet temperature=880° C
$CO_2$ recycle=100%
Pressure=20 bar absolute Hydrocarbon feed:

| | |
|---|---|
| Composition: | 80.5 mol % of butane |
| | 19.5 mol % of butene |
| Mass flow: | 57,730 kg/h |
| Inlet temperature: | 500° C. |
| Steam: | |
| Mass flow: | 180,152 kg/h |
| Inlet temperature: | 500° C. |

-continued

| | |
|---|---|
| Recirculated $CO_2$: | |
| Mass flow: | 107,833 kg/h |

The results of the simulation calculation are as follows:
Reformer Outlet:

| | |
|---|---|
| Mass flow: | 345,716 kg/h |
| Composition: | CO 18.0 mol % |
| | $CO_2$ 11.8 mol % |
| | $CH_4$ 1.4 mol % |
| | $H_2$ 38.4 mol % |
| | $H_2O$ 30.4 mol % |
| | butane 0.0 mol % |
| | butene 0.0 mol % |

Synthesis gas after $CO_2$ scrub:

| | |
|---|---|
| Mass flow: | 124,629 kg/h |
| Composition: | CO 31.1 mol % |
| | $CO_2$ 0.0 mol % |
| | $CH_4$ 2.4 mol % |
| | $H_2$ 66.5 mol % |
| | $H_2O$ 0.0 mol % |
| | butane 0.0 mol % |

The $H_2$/CO molar ratio is 2.14. A synthesis gas of this composition is well suited to the hydroformylation and hydrogenation by customary methods of the olefins obtained according to the above description. The $CH_4$ Content of the synthesis gas of 2.4 mol % is not a problem in the hydroformylation.

EXAMPLE 2

Example 1 was repeated, but the simulation was carried out for a partial oxidation of the butene-depleted $C_4$-hydrocarbon stream. The following parameters were used as a basis: temperature 1200° C., pressure 50 bar, no $CO_2$ recycle.

| | |
|---|---|
| Hydrocarbon feed: | |
| Composition: | 80.5 mol % of butane |
| | 19.5 mol % of butene |
| Mass flow: | 57,730 kg/h |
| Temperature: | 300° C. |
| Steam: | |
| Mass flow: | 36,200 kg/h |
| Temperature: | 270° C. |
| Oxygen: | |
| Mass flow: | 46,703 kg/h |
| Temperature: | 25° C. |

The simulation gave the following results:
Reactor Outlet:

| | |
|---|---|
| Composition: | 32.7 mol % of CO |
| | 4.2 mol % of $CO_2$ |
| | 0.35 mol % of $CH_4$, |

|  |  |
|---|---|
|  | 47.5 mol % of $H_2$ |
|  | 15.2 mol % of $H_2O$ |
|  | 0.0 mol % of butane |
|  | 0.0 mol % of butene |
|  | 0.0 mol % of $O_2$ |
| Mass flow: | 158,635 kg/h |
| Temperature: | 1200° C. |
| Pressure: | 50 bar |

The $H_2/CO$ molar ration is 1.455.

In addition, the synthesis gas composition of the above gas after high-temperature converting was simulated. The simulation was based on 91,646 kg/h of the above-described gas leaving the reactor outlet being conveyed in a bypass around high-temperature converting and the remainder being subjected to high-temperature converting. The simulation gave the following result:

Synthesis gas after high-temperature converting:

|  |  |
|---|---|
| Composition: | 28.1 mol % of CO |
|  | 8.8 mol % of $CO_2$ |
|  | 0.35 mol % of $CH_4$ |
|  | 52.0 mol % of $H_2$ |
|  | 10.7 mol % of $H_2O$ |
|  | 0.0 mol % of butane |
|  | 0.0 mol % of butene |
|  | 0.0 mol % of $O_2$ |

The $H_2/CO$ molar ratio of the synthesis gas after high-temperature converting is 1.85. Varying the amount passed through the bypass makes it possible to achieve other $H_2/CO$ ratios, so that the synthesis gas composition can be optimally matched to the hydroformylation and/or hydrogenation of the olefins obtained according to the above description.

We claim:

1. A process for preparing $C_9$-alcohols, which comprises
   a) providing a $C_4$-hydrocarbon stream comprising butene and butane;
   b) subjecting the $C_4$-hydrocarbon stream to oligomerization over an olefin oligomerization catalyst and fractionating the resulting reaction mixture to give an octene-containing stream and a butene-depleted $C_4$-hydrocarbon stream;
   c) subjecting the butene-depleted $C_4$-hydrocarbon stream to steam reforming or partial oxidation to give carbon monoxide and hydrogen;
   d) hydroformylating the octene-containing stream by means of carbon monoxide and hydrogen in the presence of a hydroformylation catalyst to form $C_9$-aldehydes, where the carbon monoxide used and/or the hydrogen used originate at least in part from step c); and
   e) catalytically hydrogenating the $C_9$-aldehydes by means of hydrogen.

2. A process as claimed in claim 1, wherein the hydrogen used in step e) originates at least in part from step c).

3. A process as claimed in claim 1, wherein the butene-depleted $C_4$-hydrocarbon stream is fully or partially hydrogenated prior to steam reforming.

4. A process as claimed in claim 1, wherein the steam reforming includes the use of a prereformer.

5. A process as claimed in claim 1, wherein the mixture of carbon monoxide and hydrogen obtained by steam reforming or partial oxidation of the butene-depleted $C_4$-hydrocarbon stream is subjected to high-temperature converting.

6. A process as claimed in claim 1, wherein the $C_4$-hydrocarbon stream contains from 50 to 99 mol % of butene.

7. A process as claimed in claim 1, wherein the butene-depleted $C_4$-hydrocarbon stream contains from 5 to 70 mol % of butene.

8. A process as claimed in claim 1, wherein the olefin oligomerization catalyst is a heterogeneous, nickel-containing catalyst.

9. A process for the integrated preparation of $C_9$-alcohols and $C_{10}$-alcohols, which comprises
   a) providing a $C_4$-hydrocarbon stream comprising butene and butane;
   b) hydroformylating the $C_4$-hydrocarbon stream by means of carbon monoxide and hydrogen to form $C_5$-aldehydes, so as to give a first butene-depleted $C_4$-hydrocarbon stream;
   c) subjecting the $C_5$-aldehydes to an aldol condensation; and
   d) catalytically hydrogenating the products of the aldol condensation by means of hydrogen to form $C_{10}$-alcohols;
   e) subjecting the first butene-depleted $C_4$-hydrocarbon stream to oligomerization over an olefin oligomerization catalyst and fractionating the resulting reaction mixture to give an octene-containing stream and a second butene-depleted $C_4$-hydrocarbon stream;
   f) hydroformylating the octene-containing stream by means of carbon monoxide and hydrogen in the presence of a hydroformylation catalyst to form $C_9$-aldehydes;
   g) catalytically hydrogenating the $C_9$-aldehydes by means of hydrogen;
   h) subjecting the second butene-depleted $C_4$-hydrocarbon stream to steam reforming or partial oxidation to give carbon monoxide and hydrogen which are recirculated at least in part to step b) and/or step f).

10. A process as claimed in claim 9, wherein the hydrogen used in step d) and/or step g) originates at least in part from step h).

11. A process as claimed in claim 9, wherein the second butene-depleted $C_4$-hydrocarbon stream is fully or partially hydrogenated prior to steam reforming.

12. A process as claimed in claim 9, wherein the steam reforming includes the use of a prereformer.

13. A process as claimed in claim 9, wherein the mixture of carbon monoxide and hydrogen obtained by steam reforming or partial oxidation of the second butene-depleted $C_4$-hydrocarbon stream is subjected to high-temperature converting.

14. A process as claimed in claim 9, wherein the $C_4$-hydrocarbon contains from 50 to 99 mol % of butene.

15. A process as claimed in claim 9, wherein the olefin oligomerization catalyst is a heterogeneous, nickel-containing catalyst.

* * * * *